US008889172B1

(12) United States Patent
Trollsas et al.

(10) Patent No.: US 8,889,172 B1
(45) Date of Patent: Nov. 18, 2014

(54) AMORPHOUS OR SEMI-CRYSTALLINE POLY(ESTER AMIDE) POLYMER WITH A HIGH GLASS TRANSITION TEMPERATURE

(75) Inventors: Mikael Trollsas, San Jose, CA (US); Florencia Lim, Union City, CA (US); Thierry Glauser, Redwood City, CA (US); Chris Feezor, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1562 days.

(21) Appl. No.: 12/112,949

(22) Filed: Apr. 30, 2008

(51) Int. Cl.
A61F 2/00 (2006.01)
(52) U.S. Cl.
USPC ............ 424/426; 623/1.42; 514/279
(58) Field of Classification Search
CPC ......... C08L 77/12; A61L 27/18; A61L 27/34; A61L 31/04; A61L 31/10; A61F 2/00
USPC ............ 424/426; 623/1.42; 514/279
See application file for complete search history.

(56) References Cited

U.S. PATENT DOCUMENTS

| 4,304,767 | A | 12/1981 | Heller et al. |
| 4,733,665 | A | 3/1988 | Palmaz |
| 4,800,882 | A | 1/1989 | Gianturco |
| 4,886,062 | A | 12/1989 | Wiktor |
| 4,733,665 | B1 | 1/1994 | Palmaz |
| 5,581,387 | A | 12/1996 | Cahill |
| 5,861,387 | A | 1/1999 | Labrie et al. |
| 6,503,538 | B1 | 1/2003 | Chu et al. |
| 6,703,040 | B2 | 3/2004 | Katsarava et al. |
| 7,056,591 | B1 | 6/2006 | Pacetti et al. |
| 7,166,680 | B2 * | 1/2007 | DesNoyer et al. ............ 525/425 |
| 7,202,325 | B2 | 4/2007 | Hossainy et al. |
| 7,220,816 | B2 | 5/2007 | Pacetti et al. |
| 7,771,739 | B2 * | 8/2010 | Trollsas et al. ............... 424/422 |
| 2005/0106204 | A1 | 5/2005 | Hossainy et al. |
| 2005/0112171 | A1 | 5/2005 | Tang et al. |
| 2005/0137381 | A1 | 6/2005 | Pacetti et al. |
| 2005/0208091 | A1 | 9/2005 | Pacetti |
| 2005/0245637 | A1 | 11/2005 | Tang et al. |
| 2005/0265960 | A1 | 12/2005 | Pacetti et al. |
| 2005/0271700 | A1 | 12/2005 | DesNoyer et al. |
| 2006/0089485 | A1 | 4/2006 | DesNoyer et al. |
| 2006/0093842 | A1 | 5/2006 | DesNoyer et al. |
| 2006/0115513 | A1 | 6/2006 | Hossainy |
| 2006/0142541 | A1 | 6/2006 | Hossainy |
| 2006/0147412 | A1 | 7/2006 | Hossainy et al. |

OTHER PUBLICATIONS

U.S. Appl. No. 10/816,072, Dugan et al., filed Mar. 31, 2004.
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.
De Lezo et al., *Intracoronary Ultrasound Assessment of Directional Coronary Atherectomy: Immediate and Follow-Up Findings*, JACC vol. 21, No. 2, (1993) pp. 298-307.
Design of Biopharmaceutical Properties through Prodrugs and Analogs, Editor Edward B. Roche, Book, 4 title pages (1977).
Martin et al., *Enhancing the biological activity of immobilized osteopontin using a type-1 collagen affinity coating*, Wiley Periodicals, Inc., pp. 10-19 (2004).
Moreno et al., *Macrophage Infiltration Predicts Restenosis After Coronary Intervention in Patients with Unstable Angina*, Circulation, vol. 94, No. 12, (1996) pp. 3098-3102.
Norman J. Harper, "Drug Latentiation", Progress in Drug Research, pp. 221-294 (1962).
Oikawa et al., *Mechanisms of Acute Gain and Late Lumen Loss After Atherectomy in Different Preintervention Arterial Remodeling Patterns*, The Am. J. of Cardilogy, vol. 89, (2002) pp. 505-510.
Scully et al., *Effect of a heparan sulphate with high affinity for antithrombin III upon inactivation of thrombin and coagulaton Factor Xa*, Biochem J. 262, (1989) pp. 651-658.
Sinkula et al., *Rational for Design of Biological Reversible Drug Derivatives: Prodrugs*, Journal of Pharmaceutical Sciences, Vo. 64, No. 2, pp. 181-210 (1975).
Spagnuolo et al., *Gas 1 is induced by VE-cadherin and vascular endothelial growth factor and inhibits endothelial cell apoptosis*, Blood, vol. 103, No. 8, pp. 3005-3012 (2004).
Stella et el., *Prodrugs: Do they Have Advanteges in Clinical Practice?*, Drugs, vol. 29, pp. 455-473 (1985).
Virmani et al., *Lessons From Sudden Coronary Death a Comprehensive Morphological Classification Scheme for Atherosclerotic Lesions*, Arterioscler Thromb Vasc Biol. (2000) pp. 1262-1275.
Volkel et al., *Targeting of immunolipsomes to Endothelial cells using a single-chain Fv fragment directed against human endoglin (CD105)*, Biochimica et Biophysica Acta, vol. 1663, pp. 158-166 (2004).

* cited by examiner

Primary Examiner — Suzanne Ziska
(74) Attorney, Agent, or Firm — Squire Patton Boggs (US) LLP

(57) ABSTRACT

The present invention provides an implantable device formed from an amorphous or semi-crystalline PEA polymer with a high $T_g$ and methods of making and using the same.

29 Claims, 1 Drawing Sheet

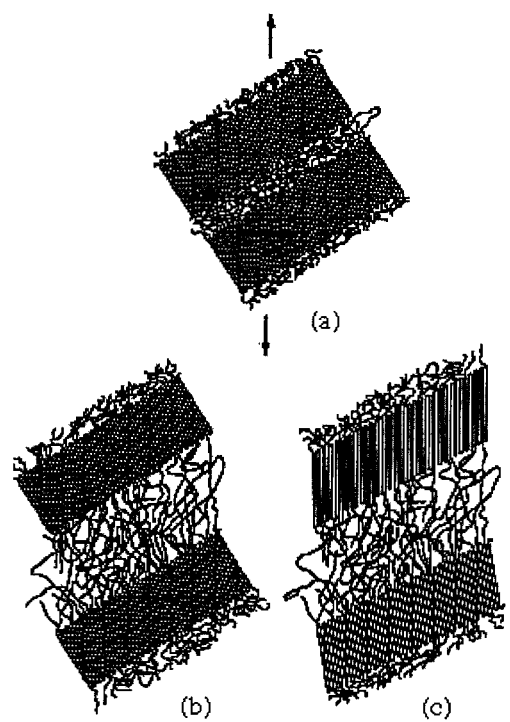

US 8,889,172 B1

AMORPHOUS OR SEMI-CRYSTALLINE POLY(ESTER AMIDE) POLYMER WITH A HIGH GLASS TRANSITION TEMPERATURE

FIELD OF THE INVENTION

The present invention relates to an amorphous or semi-crystalline poly(ester amide) polymer with a high glass transition temperature for an implantable device.

BACKGROUND OF THE INVENTION

Percutaneous coronary intervention (PCI) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion to remodel the lumen wall. The balloon is then deflated to a smaller profile to allow the catheter to be withdrawn from the patient's vasculature.

Problems associated with the above procedure include formation of intimal flaps or torn arterial linings which can collapse and occlude the blood conduit after the balloon is deflated. Moreover, thrombosis and restenosis of the artery may develop over several months after the procedure, which may require another angioplasty procedure or a surgical bypass operation. To reduce the partial or total occlusion of the artery by the collapse of the arterial lining and to reduce the chance of thrombosis or restenosis, a stent is implanted in the artery to keep the artery open. Such a stent can be a biodegradable stent.

Most biodegradable stent designs require high radial strength and are therefore prepared from highly crystalline polymers such as poly(L-lactic acid) (PLLA). Recently discoveries suggest that self-expandable stent designs may be better for therapeutic indications such as vulnerable plaque where lower radial strength is required. For these biodegradable stent designs it is important to have mechanical integrity and good shelf life stability.

The embodiments of the present invention address the above-identified needs and issues.

SUMMARY OF THE INVENTION

The present invention provides a biodegradable implantable device comprising an amorphous or semi-crystalline poly(ester amide) (PEA) polymer with a high glass-transition temperature ($T_g$). Such PEA polymers impart mechanical integrity and shelf life stability to the biodegradable implantable device. In addition, such PEA polymers have relatively fast degradation. Further, such PEA polymers can have various molecular structures and tunable physical/mechanical properties.

As used herein, the term "high $T_g$" refers to a glass transition temperature of over 55° C. In some embodiments, the term "high $T_g$" can refer to a $T_g$ of about 70° C. or higher, about 80° C. or higher (e.g., 82° C.), about 90° C. or higher, about 100° C. or higher, about 120° C. or higher, or about 150° C. or higher.

The biodegradable implantable device described herein can degrade within about 1 month, 2 months, 3 months, 4 months, 6 months, 12 months, 18 months, or 24 months after implantation. In some embodiments, the device can completely degrade or absorb within 24 months after implantation.

In some embodiments, the implantable device can include one or more other biocompatible polymers.

In some embodiments, the implantable device can include one or more bioactive agents, e.g., drug(s). Some exemplary bioactive agents that can be included in the implantable device are paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, pimecrolimus, imatinib mesylate, midostaurin, feno fibrate, prodrugs thereof, co-drugs thereof, and combinations thereof. Some other examples of the bioactive agent include siRNA and/or other oligoneucleotides that inhibit endothelial cell migration. Some further examples of the bioactive agent can also be lysophosphatidic acid (LPA) or sphingosine-1-phosphate (S1P). LPA is a "bioactive" phospholipid able to generate growth factor-like activities in a wide variety of normal and malignant cell types. LPA plays an important role in normal physiological processes such as wound healing, and in vascular tone, vascular integrity, or reproduction.

The implantable device described herein, e.g., a stent, can be implanted in a patient to treat, prevent, mitigate, or reduce a vascular medical condition, or to provide a pro-healing effect. In some embodiments, the vascular medical condition or vascular condition is a coronary artery disease (CAD) and/or a peripheral vascular disease (PVD). Some examples of such vascular medical diseases are restenosis and/or atherosclerosis. Some other examples of these conditions include thrombosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

BRIEF DESCRIPTION FO THE DRAWINGS

FIG. 1 illustrates a semi-crystalline polymer having crystalline domains (heavy blocks) and amorphous domains (waving lines).

DETAILED DESCRIPTION

The present invention provides a biodegradable implantable device comprising an amorphous or semi-crystalline poly(ester amide) (PEA) polymer with a high glass-transition temperature ($T_g$). Such PEA polymers impart mechanical integrity and shelf life stability to the biodegradable implantable device. In addition, such PEA polymers have relatively fast degradation. Further, such PEA polymers can have various molecular structures and tunable physical/mechanical properties.

As used herein, the term "amorphous" refers to the morphology attribute of a polymer having amorphous domains. Generally, an amorphous polymer only has amorphous domains and is always amorphous. A semi-crystalline polymer comprises of crystalline domains and may be amorphous domains. A semi-crystalline polymer generally has a crystallinity of 50% or below. In some embodiments, in highly oriented polymers such as fibers, a semi-crystalline polymer can have a crystallinity above 50%. Note, a semi-crystalline polymer may be in an amorphous state if the right conditions were not present during processing. Hence the crystallinity of a semi-crystalline polymer can be anywhere between 0% and the maximum crystallinity such a semi-crystalline polymer can have, with a tendency to increase over time. Semi-crystalline and amorphous describe if the polymer may crystallize or never will crystallize, respectively.

In some embodiments, the term "domain" can be referred to as "phase." Therefore, the term "crystalline domain" can be referred to as "crystalline phase." Similarly, the term "amorphous domain" can be referred to as "amorphous phase."

As used herein, the term "high $T_g$" refers to a glass transition temperature of over 55° C. In some embodiments, the term "high $T_g$" can refer to a $T_g$ of about 70° C. or higher, about 80° C. or higher (e.g., 82° C.), about 90° C. or higher, about 100° C. or higher, about 120° C. or higher, or about 150° C. or higher.

The biodegradable implantable device described herein can degrade within about 1 month, 2 months, 3 months, 4 months, 6 months, 12 months, 18 months, or 24 months after implantation. In some embodiments, the device can completely degrade or absorb within 24 months after implantation.

In some embodiments, the implantable device can include one or more other biocompatible polymers, which are described below.

In some embodiments, the implantable device can include one or more bioactive agents, e.g., drug(s). Some exemplary bioactive agents that can be included in the implantable device are paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, pimecrolimus, imatinib mesylate, midostaurin, feno fibrate, prodrugs thereof, co-drugs thereof, and combinations thereof. Some other examples of the bioactive agent include siRNA and/or other oligoneucleotides that inhibit endothelial cell migration. Some further examples of the bioactive agent can also be lysophosphatidic acid (LPA) or sphingosine-1-phosphate (S1P). LPA is a "bioactive" phospholipid able to generate growth factor-like activities in a wide variety of normal and malignant cell types. LPA plays an important role in normal physiological processes such as wound healing, and in vascular tone, vascular integrity, or reproduction.

The implantable device described herein, e.g., a stent, can be implanted in a patient to treat, prevent, mitigate, or reduce a vascular medical condition, or to provide a pro-healing effect. In some embodiments, the vascular medical condition or vascular condition is a coronary artery disease (CAD) and/or a peripheral vascular disease (PVD). Some examples of such vascular medical diseases are restenosis and/or atherosclerosis. Some other examples of these conditions include thrombosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

DEFINITIONS

Wherever applicable, the definitions to some terms used throughout the description of the present invention as provided below shall apply.

The terms "biologically degradable" (or "biodegradable"), "biologically erodable" (or "bioerodable"), "biologically absorbable" (or "bioabsorbable"), and "biologically resorbable" (or "bioresorbable"), in reference to polymers and implantable devices, are used interchangeably and refer to polymers and implantable devices that are capable of being completely or substantially completely degraded, dissolved, and/or eroded over time when exposed to physiological conditions and can be gradually resorbed, absorbed and/or eliminated by the body, or that can be degraded into fragments that can pass through the kidney membrane of an animal (e.g., a human). The process of breaking down and eventual absorption and elimination of the polymer or implantable device can be caused by, e.g., hydrolysis, metabolic processes, oxidation, enzymatic processes, bulk or surface erosion, and the like. Conversely, wherever applicable, a "biostable" polymer or implantable device refers to a polymer or implantable device that is not biodegradable.

Whenever the reference is made to "biologically degradable," "biologically erodable," "biologically absorbable," and "biologically resorbable" stent or polymers forming such stent, it is understood that after the process of degradation, erosion, absorption, and/or resorption has been completed or substantially completed, no part or substantially little part of the device will remain. Whenever the terms "degradable," "biodegradable," or "biologically degradable" are used in this application, they are intended to broadly include biologically degradable, biologically erodable, biologically absorbable, and biologically resorbable polymers or implantable device.

"Physiological conditions" refer to conditions to which an implant is exposed within the body of an animal (e.g., a human). Physiological conditions include, but are not limited to, "normal" body temperature for that species of animal (approximately 37° C. for a human) and an aqueous environment of physiologic ionic strength, pH and enzymes. In some cases, the body temperature of a particular animal may be above or below what would be considered "normal" body temperature for that species of animal. For example, the body temperature of a human may be above or below approximately 37° C. in certain cases. The scope of the present invention encompasses such cases where the physiological conditions (e.g., body temperature) of an animal are not considered "normal."

In the context of a blood-contacting implantable device, a "prohealing" drug or agent refers to a drug or agent that has the property that it promotes or enhances re-endothelialization of arterial lumen to promote healing of the vascular tissue.

As used herein, a "co-drug" is a drug that is administered concurrently or sequentially with another drug to achieve a particular pharmacological effect. The effect may be general or specific. The co-drug may exert an effect different from that of the other drug, or it may promote, enhance or potentiate the effect of the other drug.

As used herein, the term "prodrug" refers to an agent rendered less active by a chemical or biological moiety, which metabolizes into or undergoes in vivo hydrolysis to form a drug or an active ingredient thereof. The term "prodrug" can be used interchangeably with terms such as "proagent", "latentiated drugs", "bioreversible derivatives", and "congeners". N. J. Harper, Drug latentiation, *Prog Drug Res.*, 4: 221-294 (1962); E. B. Roche, Design of Biopharmaceutical Properties through Prodrugs and Analogs, Washington, D.C.: American Pharmaceutical Association (1977); A. A. Sinkula and S. H. Yalkowsky, Rationale for design of biologically reversible drug derivatives: prodrugs, *J. Pharm. Sci.*, 64: 181-210 (1975). Use of the term "prodrug" usually implies a covalent link between a drug and a chemical moiety, though some authors also use it to characterize some forms of salts of the active drug molecule. Although there is no strict universal definition of a prodrug itself, and the definition may vary from author to author, prodrugs can generally be defined as pharmacologically less active chemical derivatives that can be converted in vivo, enzymatically or nonenzymatically, to the active, or more active, drug molecules that exert a therapeutic, prophylactic or diagnostic effect. Sinkula and Yalkowsky, above; V. J. Stella et al., Prodrugs: "Do they have advantages in clinical practice?", *Drugs,* 29: 455-473 (1985).

The terms "polymer" and "polymeric" refer to compounds that are the product of a polymerization reaction. These terms are inclusive of homopolymers (i.e., polymers obtained by polymerizing one type of monomer), copolymers (i.e., polymers obtained by polymerizing two or more different types of monomers), terpolymers, etc., including random, alternating, block, graft, dendritic, crosslinked and any other variations thereof.

As used herein, the term "implantable" refers to the attribute of being implantable in a mammal (e.g., a human being or patient) that meets the mechanical, physical, chemical, biological, and pharmacological requirements of a device provided by laws and regulations of a governmental agency (e.g., the U.S. FDA) such that the device is safe and effective for use as indicated by the device. As used herein, an "implantable device" may be any suitable substrate that can be implanted in a human or non-human animal. Examples of implantable devices include, but are not limited to, self-expandable stents, balloon-expandable stents, coronary stents, peripheral stents, stent-grafts, catheters, other expandable tubular devices for various bodily lumen or orifices, grafts, vascular grafts, arterio-venous grafts, by-pass grafts, pacemakers and defibrillators, leads and electrodes for the preceding, artificial heart valves, anastomotic clips, arterial closure devices, patent foramen ovale closure devices, cerebrospinal fluid shunts, and particles (e.g., drug-eluting particles, microparticles and nanoparticles). The stents may be intended for any vessel in the body, including neurological, carotid, vein graft, coronary, aortic, renal, iliac, femoral, popliteal vasculature, and urethral passages. An implantable device can be designed for the localized delivery of a therapeutic agent. A medicated implantable device may be constructed in part, e.g., by forming the device with a material containing a therapeutic agent. The body of the device may also contain a therapeutic agent.

An implantable device can be fabricated with a material containing partially or completely a biodegradable/bioabsorbable/bioerodable polymer, a biostable polymer, or a combination thereof. An implantable device itself can also be fabricated partially or completely from a biodegradable/bioabsorbable/bioerodable polymer, a biostable polymer, or a combination thereof.

In the context of a stent, "delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

PEA with a High Glass-Transition Temperature

A poly(ester-amide) refers to a polymer that has in its backbone structure both ester and amide bonds. For example, the following formula represents a poly(ester-amide) of this invention:

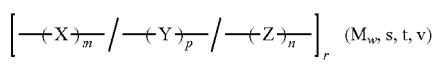

X, Y and Z refer to the constitutional units, i.e., the repeating units, of the polymer. For example, in the polymer

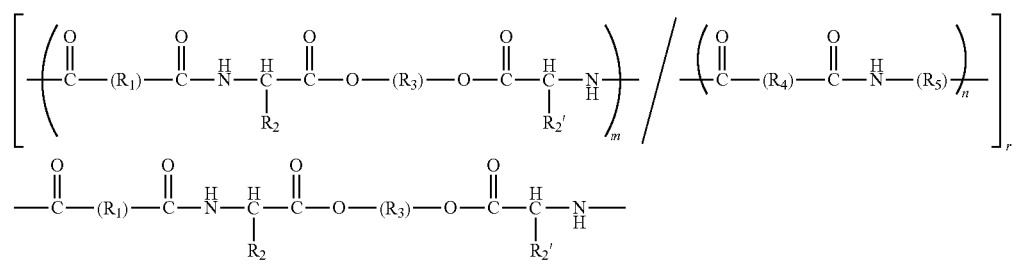

is the X constitutional unit and

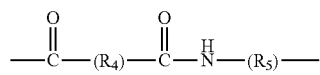

is the Z constitutional unit, Y being absent, i.e., p is 0. The constitution units themselves can be the product of the reactions of other compounds. For example, without limitation, the X constitutional unit above may comprises the reaction of an amino acid,

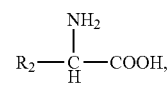

with a diol, HO—($R_3$)—OH, to give a diamino ester

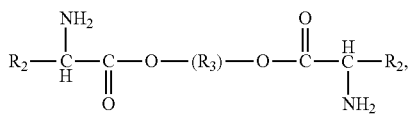

which is then reacted with a diacid,

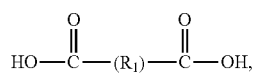

to give the constitutional unit. The amine group, the carboxylic acid group or the hydroxyl group may be "activated," i.e., rendered more chemically reactive, to facilitate the reactions if desired; such activating techniques are well-known in the art and the use of any such techniques is within the scope of this invention. A non-limiting example of the synthesis of an exemplary but not limiting X constitution unit having the above general structure is the reaction of 1,6-hexane diol with 1-leucine to give the diamino diester, which is then reacted with sebacic acid to give X. Constitutional unit Y can be obtained by the same reactions as those affording X but using one or more different reactants such that the resulting constitutional units X and Y are chemically different or Y may result from the reaction of a diacid with a tri-functional amino acid wherein two of the functional groups are capable of reacting with the diacid. As example of the foregoing would be the reaction of sebacic acid or an activated derivative thereof, with 1-lysine, i.e., 2,6-diaminohexanoic acid.

With regard to the synthesis of the poly(ester-amide)s of this invention, it will be noted that no specific reactions or reaction conditions are exemplified herein. This is because the reactions and reaction conditions both for the preparation of constitutional units and for the preparation of the final poly(ester-amide) comprise standard organic and polymer chemistry well-known to those of ordinary skill in the art and, therefore, those skilled artisans will be able to prepare any of the compounds herein without undue experimentation based on the disclosures herein.

As for the amino acids selected for the preparation of poly(ester-amide)s of this invention, any may be use; however, at present it is preferred that the amino acids be selected from the group commonly known as the standard amino acids or sometimes the proteinogenic amino acids because they are encoded by the normal genetic code. There currently are 20 standard amino acids: alanine, arginine, asparagine, aspartic acid, cysteine, glutamic acid, glutamine, glycine, histidine, isoleucine, leucine, lysine, methionine, phenyl alanine, proline, serine, threonine, tryptophan, tyrosine and valine. Relatively recently selenoadenine has been found to be incorporated into a number of proteins and is included with the above as a useful amino acid for the purposes of this invention. In naturally-occurring biological proteins, these amino acids exist primarily as l-enantiomers but for the purposes of this invention they may be used as their l- or d-enantiomers or as racemic mixtures.

In the above formula, m, p and n can be integers that represent the average number of constitutional units X, Y and Z in an uninterrupted string or, if there is more than on, block; i.e., the number of X units before a Y unit is encountered, etc. The integers m, p and n can be any number, including 0; when two of m, p and n are 0, the resulting poly(ester-amide) is a homopolymer.

In the above formula, r represents the total number of X, Y and Z units in the polymer and can be any integer from 1 to about 2500, with the proviso that the combination of m, p, n and r should provide a poly(ester-amide) that has a molecular weight within the range discussed below.

In the above formula, $M_n$ represents the number average molecular weight of a poly(ester-amide) of this invention. Again, while any molecular weight that results in a polymer that has the requisite properties to useful with the implantable medical devices of this invention, properties that are well-known to those skilled in the art, is within the scope of this invention, at present the number average molecular weight of a poly(ester-amide) of this invention is from about 10,000 Da (Daltons) to about 1,000,000 Da, preferably at present from about 20,000 Da to about 500,000 Da.

Also in the above formula, s, t and v represent the mole fraction of each of the constitutional units. Each of s, t and v is a number between 0 and 1, inclusive with s+t+v=1. It is understood that the mole fraction and the number of constitutional units are related and the designation of one will affect the other.

As noted s, t and v may each be 0, 1 or any fraction between. There are, however, certain provisos: (1) if an additional prohealing entity is present on one of the constitutional units, that constitutional unit must be at least 0.02 mol fraction of the polymer; and (2) m and p can both be 0 only if $R_5$ is selected from the group consisting of —CH(COR$_6$)CH$_2$S—, —CH(C(O)R$_6$CH$_2$O—, —CH(COR$_6$)CH(CH$_3$)O— and

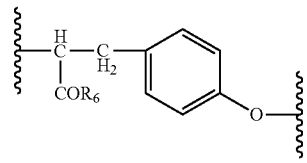

because otherwise the resulting homopolymer would not be a poly(ester-amide). Other than the preceding provisos, any values of s, t and v that provides a polymer having desirable properties for the intended use, e.g., as a drug reservoir layer, a rate-controlling layer, etc., and those skilled in the art will be readily able to make such variations and determine if the resulting polymer as the requisite properties based on the disclosures herein without undue experimentation.

The polymers of this invention may be regular alternating polymers, random alternating polymers, regular block polymers, random block polymers or purely random polymers unless expressly noted otherwise. A regular alternating polymer has the general structure: . . . x-y-z-x-y-z-x-y-z- . . . . A random alternating polymer has the general structure: . . . x-y-x-z-x-y-z-y-z-x-y- . . . , it being understood that the exact juxtaposition of the various constitution units may vary. A regular block polymer has the general structure: . . . x-x-x-y-y-y-z-z-z-x-x-x . . . , while a random block polymer has the general structure: . . . x-x-x-z-z-x-x-y-y-y-y-z-z-z-x-x-z-z-z- . . . . Similarly to the situation above regarding regular and alternating polymers, the juxtaposition of blocks, the number of constitutional units in each block and the number of blocks in block polymers of this invention are not in any manner limited by the preceding illustrative generic structures.

Constitutional unit Z, on the other hand, is the result of the reaction of a diacid with a tri-functional amino acid wherein two of the functional groups are capable of reacting with the diacid. As example would be the reaction of sebacic acid or an activated derivative thereof, with 1-lysine, 2,6-diaminohexanoic acid, the two amino groups being capable of reacting with the diacid carboxyl groups to form amides.

The poly(ester-amides) of this invention may be used as is, that is, as the product of amino acids, diacids and diols as described above because it has been found that the poly(ester-amide)s of this invention exhibit pro-healing properties in their own right. It is an aspect of this invention, however, that a poly(ester-amide) of this invention may be further modified by the attachment of an additional pro-healing moiety to an appropriate pendant group attached to the polymer backbone. By pro-healing moiety is meant a substituent group that is biocompatible and that aids in the amelioration of inflammation and/or in the endothelialization of the implantable medical device. Such substituent groups include, without limitation, stable nitroxides; phosphorylcholine, —O(CH)$_2$OP (=O)(O$^-$)OCH$_2$CH$_2$N$^+$(CH$_3$)$_3$, nitric oxide donors, nitric oxide generating catalysts that utilize nitrosothiols, oligomers of ethylene glycol or ethylene oxide; poly(ethylene glycol) and end-group modified derivatives thereof, i.e., —O(CH$_2$CH$_2$O)$_q$CH$_2$CH$_2$OR$_7$, wherein R$_7$ is selected from the group consisting of hydrogen, (1C-4C)alkyl, —C(O)

CH=CH$_2$, —C(O)C(CH$_3$)=CH$_2$ and phosphorylcholine. If R$_7$ comprises a double bond, double bonds on different polymer chainrs may be reacted with one another using UV light or a free radical initiator to give a crosslinked poly(ester-amide).

As used herein, "alkyl" refers to a straight or branched chain fully saturated (no double or triple bonds) hydrocarbon (carbon and hydrogen only) group. The alkyl groups of this invention may range from C$_1$ to C$_{12}$, preferably C$_2$ to C$_{10}$ and currently most preferably C$_3$ to C$_8$. Examples of alkyl groups include, but are not limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, and cyclohexyl. In addition, as used herein "alkyl" includes "alkylene" groups, which refer to straight or branched fully saturated hydrocarbon groups having two rather than one open valences for bonding to other groups. Examples of alkylene groups include, but are not limited to methylene, —CH$_2$—, ethylene, —CH$_2$CH$_2$—, propylene, —CH$_2$CH$_2$CH$_2$—, n-butylene, —CH$_2$CH$_2$CH$_2$CH$_2$—, sec-butylene, —CH$_2$CH$_2$CH(CH$_3$)— and the like.

As used herein, "mC to nC," wherein m and n are integers refers to the number of possible carbon atoms in the indicated group. That is, the group can contain from "m" to "n", inclusive, carbon atoms. An alkyl group of this invention may comprise from 1 to 12 carbon atoms, that is, m may be 1 and n may be 12. Of course, a particular alkyl group may be more limited, for instance without limitation, to 3 to 8 carbon atoms, in which case it would be designate as a (3C-8C)alkyl group. The numbers are inclusive and incorporate all straight or branched chain structures having the indicated number of carbon atoms. For example without limitation, a "C$_1$ to C$_4$ alkyl" group refers to all alkyl groups having from 1 to 4 carbons, that is, CH$_3$—, CH$_3$CH$_2$—, CH$_3$CH$_2$CH$_2$—, CH$_3$CH(CH$_3$)—, CH$_3$CH$_2$CH$_2$CH$_2$—, CH$_3$CH$_2$CH(CH$_3$)— and (CH$_3$)$_3$CH—.

As use herein, "cycloalkyl" refers to an alkyl group in which the end carbon atoms of the alkyl chain are covalently bonded to one another. In cycloalkyl groups, the numbers "m" to "n" refer to the number of carbon atoms in the ring so formed. Thus for instance, a (3C-8C)cycloalkyl group refers to a three, four, five, six, seven or eight member ring, that is, cyclopropane, cyclobutane, cyclopentane, cyclohexane, cycloheptane and cyclooctane.

As used herein, "bicycloalkyl" refers to two cycloalkyl-groups bonded together by a single covalent bond. An example, without limitation, of a bicycloalkyl group is bicyclohexane,

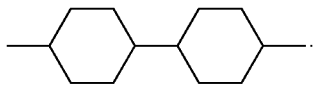

As used herein, "benzyl" refers to a phenylmethylene,

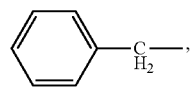

group.

As used herein, "alkenyl" refers to an alkyl group that contains in the straight or branched hydrocarbon chain one or more double bonds.

Examples of PEA polymers and the method of making a PEA polymer are described in U.S. application Ser. No. 11/486,553, which was filed Jul. 13, 2006, the teaching of which is incorporated herein in its entirety by reference. PEA polymers formed of different diacids or diols can have different T$_g$s. For example, generally, wherever applicable, decreasing the polymethylene chain length of the diol or diacid building block will increase the T$_g$. PEA polymers based on amino acids with optical rotation (e.g., L-isomers) will have higher T$_g$ than those based on the corresponding racemic amino acids (D,L-isomers). PEA polymers synthesized from optically active L-amino acids with symmetrical side substituents (e.g., valine, leucine, phenylalanine) will have higher T$_g$s than those synthesized from L-amino acids with nonsymmetrical side substituents (e.g., isoleucine). Amino acids with aromatic substituents (e.g., phenylalanine) tend to have higher T$_g$s.

In some embodiments, the PEA polymer disclosed herein comprises ester groups in its backbone that are prepared from derivatives of cyclohexandiol (C$_6$H$_{12}$O$_2$) or dicyclohexandiol (C$_{12}$H$_{22}$O$_2$). An example of such a PEA polymer has a structure shown below:

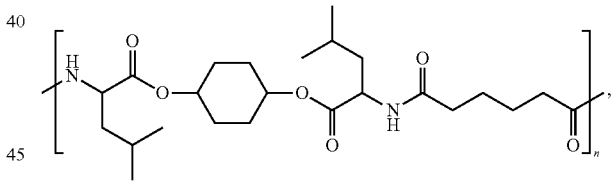

, which has a T$_g$ of about 82° C.

In some embodiments, the PEA polymer described herein comprises ester groups in its backbone that are prepared from derivatives of triethylene glycol or other oligoalkyleneoxides. An example of the PEA comprising such ester groups in the backbone can be a homopolymer or copolymer of the repeating unit below:

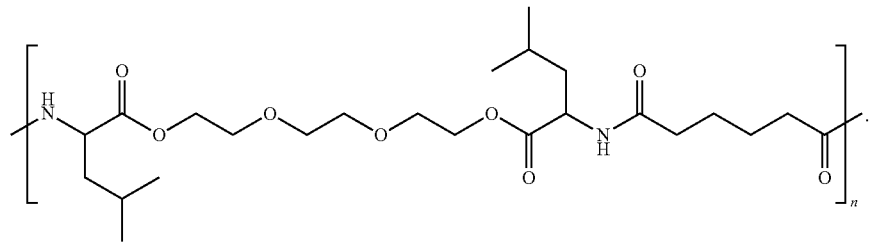

The homopolymer has a $T_g$ of about 21° C. while a random copolymer comprising the unit(s) above has a Tg over 55° C.

In some embodiments, the PEA polymer described herein comprises amide groups in its backbone that are prepared from derivatives of fumaric acid. An example of such a PEA polymer has a structure shown below:

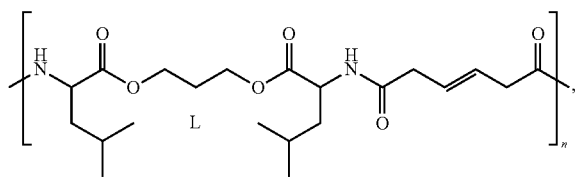

which has a $T_g$ about 120° C.

In the various formulae or unit shown above, n is an integer ranging from 1 to 100,000.

Amorphous and Crystalline Domains

The PEA polymer as described herein can have crystalline domains and/or amorphous domains and can be expressed as FIG. 1. The PEA polymer must have one or more crystalline domains having one or more crystalline polymer structures with a molar ratio sum of the crystalline domains (x) and one or more amorphous domains having one or more amorphous polymer structures with a molar ratio sum of the amorphous domains (y) that meet the definition set forth by the following equation:

$$x+y=1 \qquad \text{(equation 1)}.$$

In equation 1, x can range from 0.99 to 0, and y can each range from about 0.01 to about 1. Some exemplary values for x and y, independently, are, about 0.02, about 0.05, about 0.1, about 0.2, about 0.3, about 0.4, about 0.5, about 0.6, about 0.7, about 0.8, about 0.9, about 0.95, or about 0.98.

These PEA polymers can be random in structure or have a more block structure, or have the design of a true block copolymer. The block copolymer could be di-block, tri-block, tetra-block or penta-block co-polymers.

In some embodiments, the PEA polymer can be a semi-crystalline block copolymer. Such copolymer includes repeating units one or more monomers for providing the crystalline domains (crystalline block) and one or more monomers for providing the amorphous domains (amorphous block). Where the crystalline blocks would also provide amorphous domains and further the crystalline domain or block and/or the amorphous domain or block include repeating units from one or more different monomers, such the monomers forming the crystalline domain or block, e.g., monomers A, B, C . . . , can have different molar ratio(s), independently ranging from 0 to about 100, for example, and such monomers forming the amorphous domain or block, e.g., monomers A', B', C' . . . , can have different molar ratio(s), independently ranging from 0 to about 100, for example. However, the semi-crystalline block copolymer must have a molar ratio, x, of the crystalline domain or block and a molar ratio, y, of the amorphous domain or block as defined above. These PEA polymers have a high $T_g$ as defined above.

In some embodiments, the term "crystalline domain(s)" or "amorphous domain(s)" can be referred to as "crystalline unit(s)" or "amorphous unit(s)." In some embodiments, the term "repeating unit(s)" can also be referred to as "crystalline unit(s)" or "amorphous unit(s)."

Biologically Active Agents

In some embodiments, the implantable device described herein can optionally include at least one biologically active ("bioactive") agent. The at least one bioactive agent can include any substance capable of exerting a therapeutic, prophylactic or diagnostic effect for a patient.

Examples of suitable bioactive agents include, but are not limited to, synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. The bioactive agents could be designed, e.g., to inhibit the activity of vascular smooth muscle cells. They could be directed at inhibiting abnormal or inappropriate migration and/or proliferation of smooth muscle cells to inhibit restenosis.

In certain embodiments, optionally in combination with one or more other embodiments described herein, the implantable device can include at least one biologically active agent selected from antiproliferative, antineoplastic, antimitotic, anti-inflammatory, antiplatelet, anticoagulant, antifibrin, antithrombin, antibiotic, antiallergic and antioxidant substances.

An antiproliferative agent can be a natural proteineous agent such as a cytotoxin or a synthetic molecule. Examples of antiproliferative substances include, but are not limited to, actinomycin D or derivatives and analogs thereof (manufactured by Sigma-Aldrich, or COSMEGEN available from Merck) (synonyms of actinomycin D include dactinomycin, actinomycin IV, actinomycin $I_1$, actinomycin $X_1$, and actinomycin $C_1$); all taxoids such as taxols, docetaxel, and paclitaxel and derivatives thereof; all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Examples of rapamycin derivatives include, but are not limited to, 40-O-(2-hydroxy)ethyl-rapamycin (trade name everolimus from Novartis), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus, manufactured by Abbott Labs.), prodrugs thereof, co-drugs thereof, and combinations thereof.

An anti-inflammatory drug can be a steroidal anti-inflammatory drug, a nonsteroidal anti-inflammatory drug (NSAID), or a combination thereof. Examples of anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Alternatively, the anti-inflammatory agent can be a biological inhibitor of pro-inflammatory signaling molecules. Anti-inflammatory biological agents include antibodies to such biological inflammatory signaling molecules.

In addition, the bioactive agents can be other than antiproliferative or anti-inflammatory agents. The bioactive agents can be any agent that is a therapeutic, prophylactic or diagnostic agent. In some embodiments, such agents can be used in combination with antiproliferative or anti-inflammatory agents. These bioactive agents can also have antiproliferative and/or anti-inflammatory properties or can have other properties such as antineoplastic, antimitotic, cystostatic, antiplatelet, anticoagulant, antifibrin, antithrombin, antibiotic, antiallergic, and/or antioxidant properties.

Examples of antineoplastics and/or antimitotics include, but are not limited to, paclitaxel (e.g., TAXOL® available from Bristol-Myers Squibb), docetaxel (e.g., Taxotere® from Aventis), methotrexate, azathioprine, vincristine, vinblastine, fluorouracil, doxorubicin hydrochloride (e.g., Adriamycin® from Pfizer), and mitomycin (e.g., Mutamycin® from Bristol-Myers Squibb).

Examples of antiplatelet, anticoagulant, antifibrin, and antithrombin agents that can also have cytostatic or antiproliferative properties include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX (from Biogen), calcium channel blockers (e.g., nifedipine), colchicine, fibroblast growth factor (FGF) antagonists, fish oil (e.g., omega 3-fatty acid), histamine antagonists, lovastatin (a cholesterol-lowering drug that inhibits HMG-CoA reductase, brand name Mevacor® from Merck), monoclonal antibodies (e.g., those specific for platelet-derived growth factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetics, 4-amino-2,2,6,6-tetramethylpiperidine-1-oxyl (4-amino-TEMPO), estradiol, anticancer agents, dietary supplements such as various vitamins, and a combination thereof.

Examples of cytostatic substances include, but are not limited to, angiopeptin, angiotensin converting enzyme inhibitors such as captopril (e.g., Capoten® and Capozide® from Bristol-Myers Squibb), cilazapril and lisinopril (e.g., Prinivil® and Prinzide® from Merck).

Examples of antiallergic agents include, but are not limited to, permirolast potassium. Examples of antioxidant substances include, but are not limited to, 4-amino-2,2,6,6-tetramethylpiperidine-1-oxyl (4-amino-TEMPO). Other bioactive agents include anti-infectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and anti-arrhythmics; antihypertensives; diuretics; vasodilators including general coronary vasodilators; peripheral and cerebral vasodilators; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Other biologically active agents that can be used include alpha-interferon, genetically engineered epithelial cells, tacrolimus and dexamethasone.

A "prohealing" drug or agent, in the context of a blood-contacting implantable device, refers to a drug or agent that has the property that it promotes or enhances re-endothelialization of arterial lumen to promote healing of the vascular tissue. The portion(s) of an implantable device (e.g., a stent) containing a prohealing drug or agent can attract, bind and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization can promote the endothelialization at a rate faster than the loss of mechanical properties of the stent.

The prohealing drug or agent can be dispersed in the body of the bioabsorbable polymer substrate or scaffolding. The prohealing drug or agent can also be dispersed within a bioabsorbable implantable device (e.g., a stent).

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing drug or agent can be an endothelial cell (EDC)-binding agent. In certain embodiments, the EDC-binding agent can be a protein, peptide or antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways. S. M. Martin, et al., *J. Biomed. Mater. Res.,* 70A:10-19 (2004). Endothelial cells can be selectively targeted (for the targeted delivery of immunoliposomes) using scFv A5. T. Volkel, et al., *Biochimica et Biophysica Acta,* 1663:158-166 (2004). Junction membrane protein vascular endothelial (VE)-cadherin has been shown to bind to endothelial cells and down regulate apoptosis of the endothelial cells. R. Spagnuolo, et al., *Blood,* 103:3005-3012 (2004).

In a particular embodiment, the EDC-binding agent can be the active fragment of osteopontin, (Asp-Val-Asp-Val-Pro-Asp-Gly-Asp-Ser-Leu-Ala-Try-Gly). Other EDC-binding agents include, but are not limited to, EPC (epithelial cell) antibodies, RGD peptide sequences, RGD mimetics, and combinations thereof.

In further embodiments, the prohealing drug or agent can be a substance or agent that attracts and binds endothelial progenitor cells. Representative substances or agents that attract and bind endothelial progenitor cells include antibodies such as CD-34, CD-133 and vegf type 2 receptor. An agent that attracts and binds endothelial progenitor cells can include a polymer having nitric oxide donor groups.

The foregoing biologically active agents are listed by way of example and are not meant to be limiting. Other biologically active agents that are currently available or that may be developed in the future are equally applicable.

In a more specific embodiment, optionally in combination with one or more other embodiments described herein, the implantable device of the invention comprises at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, progenitor cell-capturing antibodies, prohealing drugs, prodrugs thereof, co-drugs thereof, and a combination thereof. In a particular embodiment, the bioactive agent is everolimus. In another specific embodiment, the bioactive agent is clobetasol.

An alternative class of drugs would be p-para-α-agonists for increased lipid transportation, examples include feno fibrate.

In some embodiments, optionally in combination with one or more other embodiments described herein, the at least one biologically active agent specifically cannot be one or more of any of the bioactive drugs or agents described herein.

Method of Fabricating Implantable Device

Other embodiments of the invention, optionally in combination with one or more other embodiments described herein, are drawn to a method of fabricating an implantable device.

In some embodiments, to form an implantable device formed from a polymer, a polymer or copolymer optionally including at least one bioactive agent described herein can be formed into a polymer construct, such as a tube or sheet that can be rolled or bonded to form a construct such as a tube. An implantable device can then be fabricated from the construct. For example, a stent can be fabricated from a tube by laser machining a pattern into the tube. In another embodiment, a polymer construct can be formed from the polymeric material of the invention using an injection-molding apparatus.

Any of the above described PEA polymers can be used to form an implantable device. Non-limiting examples of the PEA polymer described herein can be a homopolymer or copolymer comprising any of the formulae or unit below:

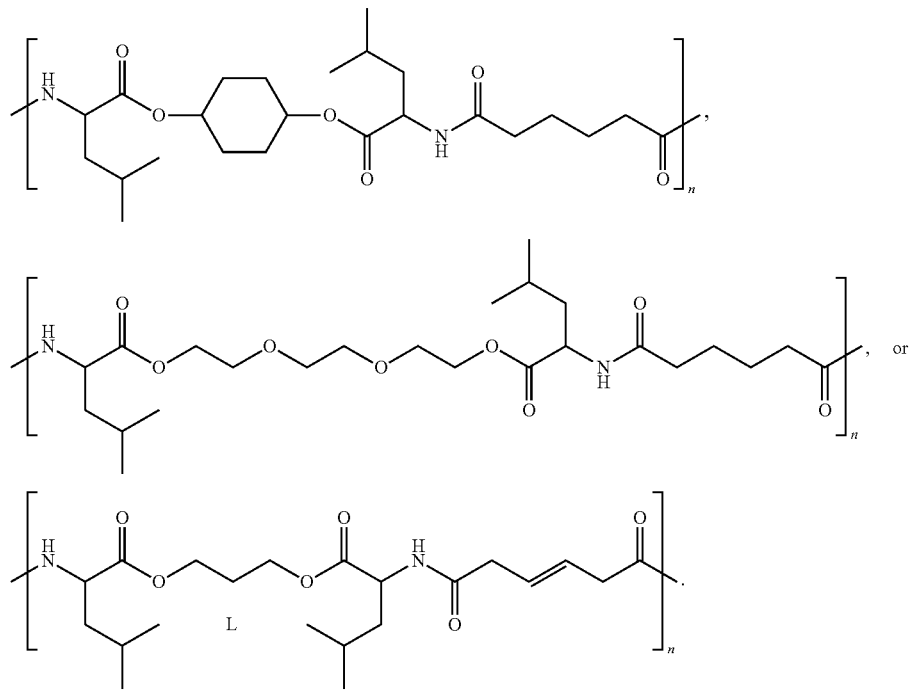

In the various formulae or unit shown above, n is an integer ranging from 1 to 100,000.

The implantable device formed herefrom can include a bioactive agent described above. In some embodiments, the implantable device can specifically exclude one or more bioactive agents described above.

Method of Treating or Preventing Disorders

An implantable device according to the present invention can be used to treat, prevent or diagnose various conditions or disorders. Examples of such conditions or disorders include, but are not limited to, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. A portion of the implantable device or the whole device itself can be formed of the material, as described herein.

In certain embodiments, optionally in combination with one or more other embodiments described herein, the inventive method treats, prevents or diagnoses a condition or disorder selected from atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. In a particular embodiment, the condition or disorder is atherosclerosis, thrombosis, restenosis or vulnerable plaque.

In one embodiment of the method, optionally in combination with one or more other embodiments described herein, the implantable device is formed of a material containing at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy) ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, progenitor cell-capturing antibodies, prohealing drugs, fenofibrate, prodrugs thereof, co-drugs thereof, and a combination thereof.

In certain embodiments, optionally in combination with one or more other embodiments described herein, the implantable device used in the method is selected from stents, grafts, stent-grafts, catheters, leads and electrodes, clips, shunts, closure devices, valves, and particles. In a specific embodiment, the implantable device is a stent.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true spirit and scope of this invention.

The invention claimed is:

1. A biodegradable implantable device, comprising an amorphous or semi-crystalline poly(ester amide) (PEA) polymer having a high glass-transition temperature ($T_g$),
wherein the PEA polymer is a homo or copolymer comprising a block or unit selected from

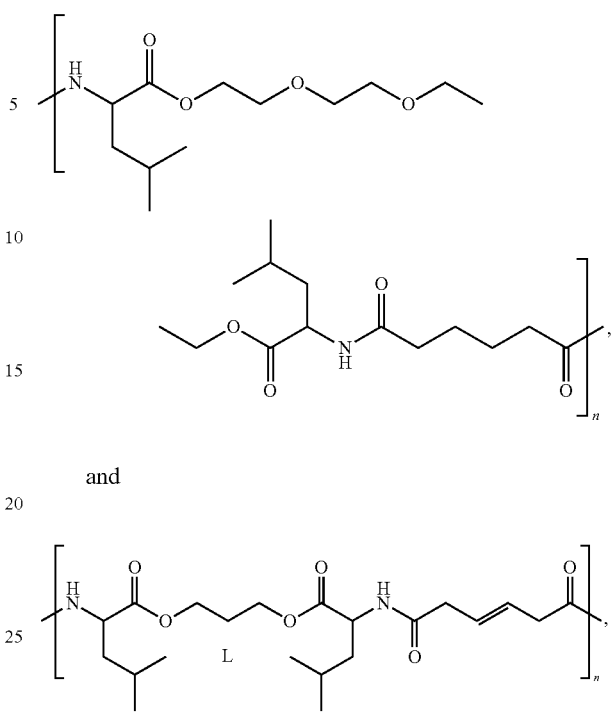

and wherein n is an integer ranging from 1 to 100,000.

2. The biodegradable implantable device of claim 1, wherein the PEA polymer has a $T_g$ is above 50° C.

3. The biodegradable implantable device of claim 1, wherein the PEA polymer has a $T_g$ is about 80° C. or higher.

4. The biodegradable implantable device of claim 1, wherein the PEA polymer has a $T_g$ is about 120° C. or higher.

5. The biodegradable implantable device of claim 1, further comprising a bioactive agent.

6. The bioactive implantable device of claim 1, further comprising a bioactive agent selected from paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy) ethoxy]ethyl-rapamycin, and 40-O-tetrazole-rapamycin, 40-epi-(N1-tetrazolyl)-rapamycin (ABT-578), γ-hiridun, clobetasol, pimecrolimus, imatinib mesylate, midostaurin, fenofibrate, prodrugs thereof, co-drugs thereof, and combinations thereof.

7. The biodegradable implantable device of claim 1, further comprising everolimus.

8. The biodegradable implantable device of claim 1, which is a stent.

9. The biodegradable implantable device of claim 6, which is a stent.

10. The biodegradable implantable device of claim 1, which completely degrades or absorbs within 24 months after implantation.

11. The biodegradable implantable device of claim 1, which completely degrades or absorbs within 12 months after implantation.

12. The biodegradable implantable device of claim 1, which completely degrades or absorbs within 6 months after implantation.

13. A method of fabricating a device, comprising:
providing coating composition comprising an amorphous or semi-crystalline poly(ester amide) (PEA) polymer having a high glass-transition temperature ($T_g$), and
forming a biodegradable implantable device comprising the amorphous or semi-crystalline PEA polymer,
wherein the PEA polymer is a homo or copolymer comprising a block or unit selected from

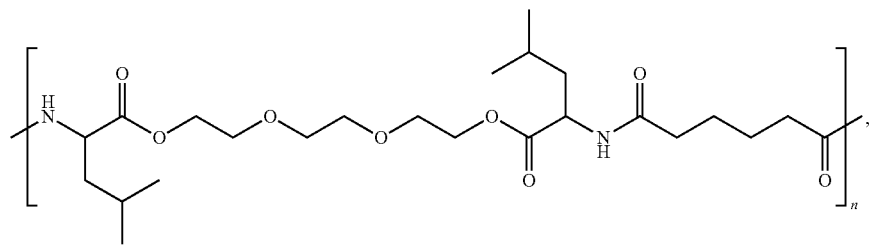

and

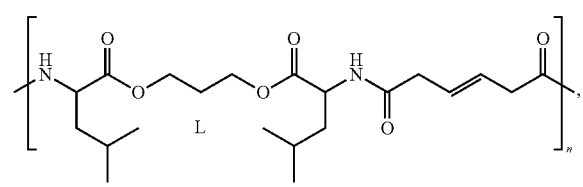

wherein n is an integer ranging from 1 to 100,000.

14. The method of claim 13, wherein the PEA polymer has a $T_g$ is above 50° C.

15. The method of claim 13, wherein the PEA polymer has a $T_g$ is about 80° C. or higher.

16. The method of claim 13, wherein the PEA polymer has a $T_g$ is about 120° C. or higher.

17. The method of claim 13, wherein the coating composition further comprises a bioactive agent.

18. The method of claim 13, wherein the coating composition further comprises a bioactive agent selected from paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, pimecrolimus, imatinib mesylate, midostaurin, feno fibrate, prodrugs thereof, co-drugs thereof, and combinations thereof.

19. The method of claim 13, wherein the coating composition further comprises everolimus.

20. The method of claim 13, wherein the implantable device is a stent.

21. The method of claim 18, wherein the implantable device is a stent.

22. The method of claim 13, wherein the implantable device degrades or absorbs within 24 months after implantation.

23. The method of claim 13, wherein the implantable device completely degrades or absorbs within 12 months after implantation.

24. The method of claim 13, wherein the implantable device completely degrades or absorbs within 6 months after implantation.

25. A method of treating, preventing, or ameliorating a vascular medical condition, comprising implanting in a patient a biodegradable implantable device comprising a poly(ester amide) (PEA) polymer having a high glass-transition temperature ($T_g$) according to claim 1, wherein the vascular medical condition is selected from restenosis, atherosclerosis, thrombosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

26. The biodegradable implantable device of claim 1, wherein the PEA polymer further comprises:

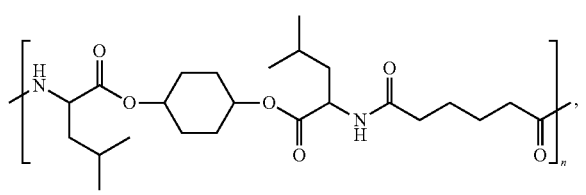

wherein n is an integer ranging from 1 to 100,000.

27. The method of claim 13, wherein the PEA polymer further comprises:

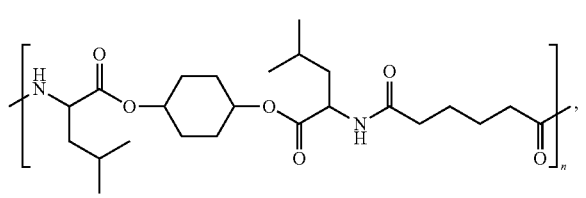

wherein n is an integer ranging from 1 to 100,000.

28. A biodegradable implantable device, comprising an amorphous or semi-crystalline poly(ester amide) (PEA) polymer having a high glass-transition temperature ($T_g$),
wherein the PEA polymer is a homo or copolymer comprising a block or unit selected from

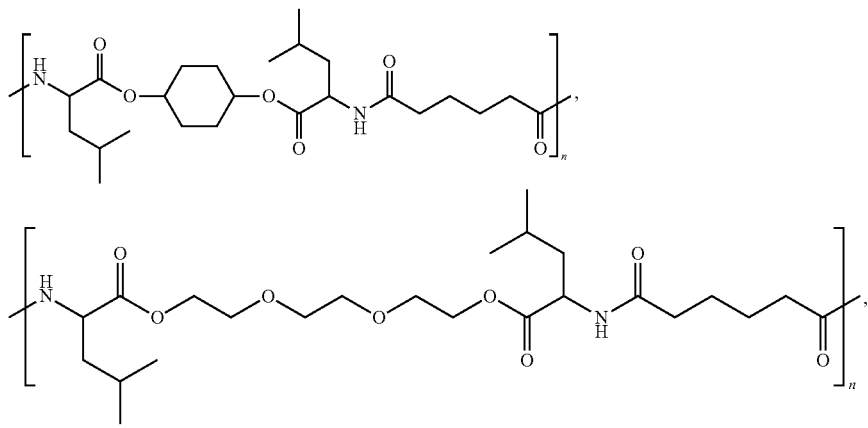

and

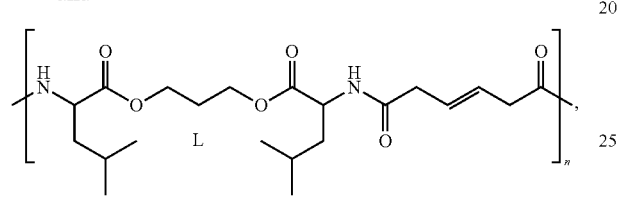

wherein n is an integer ranging from 1 to 100,000.

29. A method of fabricating a device, comprising:
providing coating composition comprising an amorphous or semi-crystalline poly(ester amide) (PEA) polymer having a high glass-transition temperature ($T_g$), and
forming a biodegradable implantable device comprising the amorphous or semi-crystalline PEA polymer,
wherein the PEA polymer is a homo or copolymer comprising a block or unit selected from

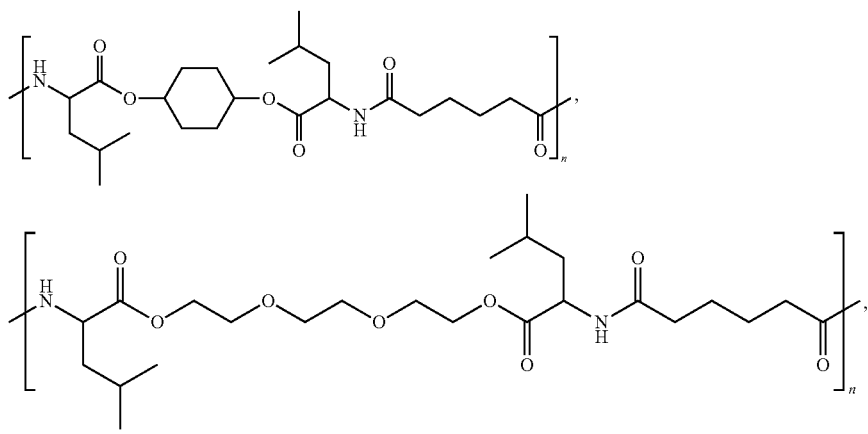

and

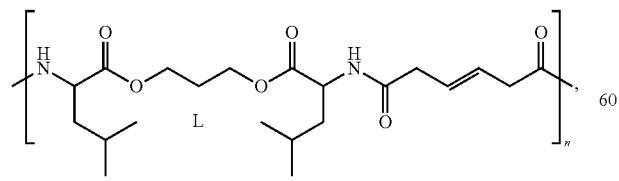

wherein n is an integer ranging from 1 to 100,000.

* * * * *